United States Patent
Mussoff et al.

(10) Patent No.: US 9,319,483 B2
(45) Date of Patent: Apr. 19, 2016

(54) ASYNCHRONOUS OPEN TASK FOR OPERATING ROOM CONTROL SYSTEM

(71) Applicant: Karl Storz Imaging, Inc., Goleta, CA (US)

(72) Inventors: David Mussoff, Broomfield, CO (US); Alexander Hau, Tuttlingen (DE); Jean-Marc Bonnaudet, Munich (DE); Christoph Hiltl, Bohlingen (DE)

(73) Assignee: Karl Storz Imaging, Inc., Goleta, CA (US)

( * ) Notice: Subject to any disclaimer, the term of this patent is extended or adjusted under 35 U.S.C. 154(b) by 620 days.

(21) Appl. No.: 13/675,427

(22) Filed: Nov. 13, 2012

(65) Prior Publication Data
US 2014/0137009 A1    May 15, 2014

(51) Int. Cl.
*G06F 13/00* (2006.01)
*H04L 29/06* (2006.01)
*G06F 19/00* (2011.01)

(52) U.S. Cl.
CPC ............... *H04L 67/42* (2013.01); *G06F 19/32* (2013.01); *G06F 19/321* (2013.01); *G06F 19/3481* (2013.01)

(58) Field of Classification Search
None
See application file for complete search history.

(56) References Cited

U.S. PATENT DOCUMENTS

| | | | |
|---|---|---|---|
| 5,788,688 A | 8/1998 | Bauer et al. | |
| 8,069,420 B2 | 11/2011 | Plummer | |
| 8,884,958 B2 * | 11/2014 | Tsukagoshi | A61B 5/055 345/419 |
| 2003/0171740 A1 | 9/2003 | Stiller et al. | |
| 2004/0024384 A1 | 2/2004 | Novak | |
| 2004/0230094 A1 * | 11/2004 | Nakamura | 600/101 |
| 2005/0284491 A1 * | 12/2005 | Tashiro et al. | 128/897 |
| 2006/0152516 A1 * | 7/2006 | Plummer | 345/538 |
| 2007/0050828 A1 * | 3/2007 | Renzi et al. | 725/93 |
| 2009/0268986 A1 * | 10/2009 | Holstein et al. | 382/305 |
| 2010/0254616 A1 * | 10/2010 | Abdo et al. | 382/232 |
| 2010/0295870 A1 * | 11/2010 | Baghdadi et al. | 345/650 |
| 2011/0249125 A1 * | 10/2011 | Wallack et al. | 348/163 |
| 2012/0274586 A1 * | 11/2012 | Southworth et al. | 345/173 |

OTHER PUBLICATIONS

OR 1 (R) Essential Drawings Drawn By: SS Dated: Sep. 9, 2008 13 pages.
OR1(R) Essential—Instruction Manual; (c) 2009 Karl Storz Endoscopy-America, Inc.; 36 pages.

* cited by examiner

*Primary Examiner* — Matt Kim
*Assistant Examiner* — Daniel Samwel
(74) *Attorney, Agent, or Firm* — Whitmyer IP Group LLC

(57) ABSTRACT

An operating room control system that includes a computer, a visualization device, an input device and a storage device where the user can open a first medical procedure session on the operating room control system by means of the input device, image data is generated by the visualization device and routed/saved to the storage device, and a second medical procedure session may be opened while the image data from the first medical procedure session is being routed/saved to the storage device. The first medical procedure session may then be closed after the image data from the first medical procedure session has been routed/saved to the storage device.

17 Claims, 7 Drawing Sheets

ASYNCHRONOUS OPEN TASK FOR OPERATING ROOM CONTROL SYSTEM

FIELD OF THE INVENTION

The invention relates to the field of medical image routing, and in particular to a system for routing medical images from an operating room system that allows the operating room system to perform multiple other tasks while routing medical image data to one or more other medical systems.

BACKGROUND OF THE INVENTION

A variety of operating room systems are known for performing both diagnostic and surgical procedures. In particular, systems have been provided that allow a surgeon to perform a procedure with a wide range of medical and operating room equipment. This equipment ranges from visual imaging tools (e.g., endoscopes, cameras, etc.) and systems, to medical devices (e.g. tools for cutting, grasping, extracting, irrigating, etc.), and other operating room equipment.

These systems have provided for improved and more efficient surgical procedures. However, medical costs continue to increase as do the cost associated with the purchasing and maintaining of medical equipment. Accordingly, it is advantageous to minimize the number of different operating control room systems purchased for a hospital. For example, it is more cost efficient to have one operating room control system and schedule multiple procedures at different times during the day than to have multiple operating room control systems that sit idle for portions of the day.

Likewise, as the number of individuals seeking medical procedures continue to increase, it is important to closely schedule procedures to maximize the number of medical procedures that can be performed on an operating room control system during a day.

In particular, operating room visualization equipment has been provided that allows for visualization of the interior of an organ or joint while a surgeon is conducting a procedure. These visualization systems allow for a surgeon to view, typically on a surgical monitor placed either in or adjacent to the sterile environment, a location inside the body where the procedure is being performed. These systems have further allowed for the recording of still pictures and video recordings of the area and procedure. Not only have the surgeon and those in the operating room been able to view the surgical site on the surgical monitor, but systems have further provided for the transfer of visualization information via a network connection to remote locations from the operating room. In this manner, individuals have had the capacity to view a surgical procedure from different locations. This has proved to be a very helpful educational tool (e.g. medical students can view a medical procedure from a class room) and has allowed for specialists to view the surgical procedure from a distance to provide expert analysis and input to the surgeon.

U.S. Pat. No. 8,069,420 to Roderick Plummer (the Plummer patent) discloses a system that allows for the identification of video collecting sources and the video destinations such that the surgeon need only select the icon on the touchscreen corresponding to the video input device and select the icon on the touchscreen corresponding to the desired destination and the video is routed to the desired destination.

The Plummer patent was a very large leap over prior art systems in that it allowed the surgeon control via a very user friendly interface to route medical imaging data by simply selecting the icon on the touch screen.

However, while audio-visual capabilities have continued to be developed and improved, the image data that is generated by the visualization equipment tends to be quite large. These image files (videos of the medical procedure) can be saved to many differing locations including a local DVD drive or to a remote storage device whether on the hospital information system or to the surgeon's computer in his/her office.

A major problem with current systems is that when the operating room control system is initiated and in use for a current medical procedure, the current medical procedure must be completed before the operating room control system can be initiated for the next medical procedure. With the advent of recording the surgical procedure to one or more storage devices, it has become a problem that the medical personnel have to wait for the image data to be transferred and completed before the operating room control system can be set up for the next medical procedure. This has lead to the medical team sitting around for large periods of time while the operating room control system writes the image data to, for example, a DVD.

SUMMARY OF THE INVENTION

Accordingly, it is an object of the present invention to provide an operating room control system that minimizes the time between medical procedures.

It is a further object of the present invention to provide an operating room system that allows the system to be configured for a second medical procedure before the first medical procedure has been closed out on the system.

It is another object of the present invention to provide an operating room control system that allows image data recorded in a first medical procedure to be routed to a storage device and simultaneously allows the operating room control system to be configured for a second medical procedure.

In accordance with aspects of the invention, an operating room control system is provided that allows for image data (whether from a video endoscope or video laryngoscope, etc.) to be routed to and saved on a storage device both during and after a medical procedure has been performed. Typically the image data file(s) generated by an imaging device can be quite large (many megabytes) and the routing and saving of this image data occurs after the medical procedure is completed. Some of the data transfer may occur during the procedure itself, but quite often the writing of the image data to, for example, a DVD occurs after the medical procedure has finished. The procedure cannot be viewed as "completed" by the operating room control system until all the image data has been properly routed and saved. Current operating room control systems will not allow the operating room control system to be configured for a second medical procedure until the first medical procedure is "completed" including the routing and saving of all the image data.

The present invention allows the operating room control system to be configured for a second medical procedure prior to the first medical procedure being "completed" (e.g., prior to the routing and saving of all the image data). This saves a significant amount of time for the hospital personnel as many hours of previous "down time" (e.g. waiting for the transfer of the image data) can now be efficiently used for the configuring and setting up of the operating room control system. This will become more and more important with the ability to completely configure operating room control systems according to a surgeon's preferences.

In one aspect of the invention, the operating room control system includes a computer, a storage accessible by the computer, a visualization device generating image data, a touchscreen controller connected to the computer for controlling the system, and a display for displaying the image data. The system provides for initiation of a first procedure where the operating room control system is configured for the first procedure. Configuration may include configuration of the system to function in a predetermined manner according to the surgeon's preferences. This may include the set up of the touchscreen, the setting of various equipment, the presentation of image data from the visualization device, and the like. The system further provides for "completion" of the first medical procedure when all of the functions relating to the first medical procedure are completed on the operating room control system. Finally, the system provides for the configuration of the operating room control system for a second medical procedure prior to the operating room control system "completing" the first medical procedure.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The terms "process" and "processing" as used herein each mean an action or a series of actions including, for example, but not limited to, the continuous or non-continuous, synchronous or asynchronous, direction of data, modification of data, formatting and/or conversion of data, tagging or annotation of data, measurement, comparison and/or review of data, and may or may not comprise a program.

In one embodiment an operating room control system is provided comprising a computer having a network connection, a storage accessible by the computer, and an interface coupled to the computer. The system also comprises an input device coupled to the interface, a visualization device coupled to the interface and generating image data, and a surgical display coupled to the interface and displaying the image data. The system is provided such that software executes on the computer where a first medical procedure session is opened and the operating room control system is configured for the first medical procedure, and the image data is routed to and saved on the storage. The system is further provided such that software executes on the computer where a second medical procedure session is opened and the operating room control system is configured for the second medical procedure while the image data is being saved on the storage.

In another embodiment a method is provided for configuring an operating room control system including a computer connected to a network and a storage accessible by the computer, an interface connected to the computer, and an input device and a visualization device both connected to the interface. The method comprises the steps of executing software on the computer to open a first medical procedure session on the operating room control system, and configuring the operating room control system based on the type of medical procedure to be performed and according to predefined configuration preferences. The method further comprises the steps of generating image data with the visualization device, routing the image data to the storage, and saving the image data on to the storage. Finally, the method includes the steps of executing software on the computer to open a second medical procedure session on the operating room control system while simultaneously saving the image data on the storage, and executing software on the computer to close a first medical procedure session on the operating room control system when the image data has been saved on the storage.

Other objects of the invention and its particular features and advantages will become more apparent from consideration of the following drawings and accompanying detailed description.

DETAILED DESCRIPTION OF THE INVENTION

Figure 1:
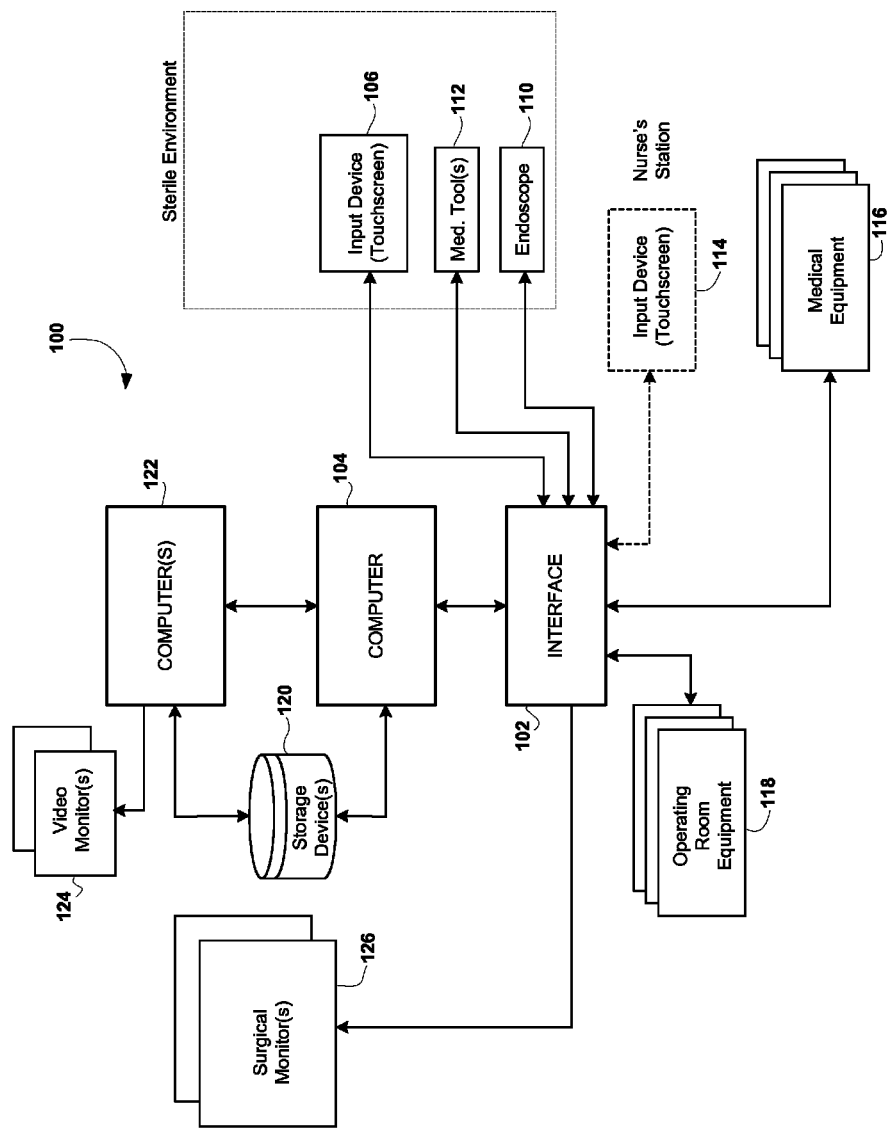
FIG. 1 is block diagram of one advantageous embodiment of the present invention.

Referring now to the drawings, wherein like reference numerals designate corresponding structure throughout the views.

FIG. 1 is a block diagram illustrating an advantageous embodiment of operating room control system 100. In this embodiment, operating room control system 100 is shown including interface 102, which is coupled to computer 104. The interface 102 would typically be positioned or located in the operating room in proximity to the various equipment connected thereto and in one embodiment would be rack-mounted. It is further understood that computer 104 may also be located in the operating room and rack-mounted, however, this is not required as the interface 102 could be coupled to computer 104 via a network connection.

Connected to interface 102 is input device (touchscreen) 106, which provides an interface for the user to control and interface with operating room control system 100. Input device 106 is shown positioned in the sterile environment and is accessible by, for example, a surgeon performing a procedure.

Also illustrated in FIG. 1 is endoscope 110 and medical tool(s) 112 connected to interface 102. Endoscope 110 may comprise virtually any type of video endoscope that allows for visualization of a surgical site inside of the body and may be flexible or rigid and have a detachable or integral camera. It is further contemplated that endoscope 110 may utilize a wired or wireless connection to interface 102 and have a CCD or CMOS imager (not shown) positioned on the endoscope for converting received light to a digital image stream.

Likewise, medical tool(s) 112 may comprise a wide variety of medical tools used by the surgeon including, but not limited to: catheterization devices, bi-polar cutting devices, lasers, rotating cutting devices, cell collection devices, suction devices and the like. It is understood that many of these medical tools 112 may be manufactured by different companies and therefore the command and control signals for each of the medical tools may differ. Interface 102 is provided to interface between the numerous differing types of signal formats such that the user may control a medical tool(s) from the touchscreen 106 if desired. Additionally, the user has the option to control the endoscope 110 from the touchscreen 106 if desired. It should be noted that many, if not all of the medical tools 112 and endoscope 110 have controls positioned directly thereon such that the surgeon may control the medical tool(s) 112 and endoscope 110 by manipulating the control interface on the device itself as opposed to the touchscreen 106.

A second input device (touchscreen) 114 is also illustrated in FIG. 1, which is provided with a notation (nurse's station) indicating that this input device 114 may be located at the nurse's station. The broken line indicates that this second input device is an optional feature. It is contemplated that input device 114 may be redundant to and provide all the functionality of input device 106 but is positioned outside of the sterile environment. In this manner, a nurse has the ability to make an adjustment based on the surgeon's direction if, for example, it is not convenient for the surgeon to do so on input device 106. It is also contemplated that additional features or a different configuration may be provided for input device 114 as opposed to input device 106.

Medical equipment 116 is illustrated having a number of boxes to indicate that there may be a plurality of medical equipment 116 connected to interface 102. Typically medical equipment 116 will be rack-mounted on a rack with wheels, or mounted on positionable boom-arms suspended from the operating room ceiling, allowing for the equipment to be placed conveniently and in proximity to the sterile environment. Medical equipment 116 will vary depending on the procedure being performed, however, to provide some context to the types of equipment that medical equipment 116 may comprise, a non-exhaustive list is provided including: insufflation equipment, irrigation equipment, vacuum equipment and the like. It should be understood that a great number of different types of equipment may be used depending upon the procedure to be performed. Like the medical tool(s) 112, it is contemplated that medical equipment 116 will be equipment manufactured by many different companies and therefore have command and control signals with diverse formats and requirements. Accordingly, interface 102 is provided to send and receive data to and from the various medical equipment 116 such that the medical equipment 116 may be controlled from either input device 106 or input device 114. It is further understood that the various medical equipment 116 may be directly controlled by interfaces on the front panels of medical equipment 116 by, for example, a nurse at the nurse's station under direction of the surgeon.

Also shown in FIG. 1 is operating room equipment 118 connected to interface 102. Like medical equipment 116, operating room equipment 118 is controllable from either input device 106 or input device 114. Operating room equipment 118 may comprise a wide variety of equipment that may be desirable to control by the surgeon or nurse including, but not limited to, the operating room lights, the operating room blinds or shades, and the positioning of the operating room table. Operating room equipment 118 may also comprise hospital system including PACS, HIS and RIS, and remote image storage systems. For example, it may be advantageous for the surgeon (or nurse) to access the patient's medical records to verify treatment, conditions or status prior to or during the procedure. Likewise, the surgeon may desire to access a medical image (e.g., an MRI or x-ray) of the patient before or during a procedure. All of these options are available to the user via the touchscreen.

Still further, storage device(s) 120 is shown connected to computer 104 and/or computer(s) 122. Storage device(s) 120 may comprise virtually any type of digital storage device including solid state hard drive devices, magnetic hard drives devices, optical drive devices, removable storage devices and the like. For example, it may be desired to record a part or all of the procedure from the video endoscope 110 to a DVD inserted into computer 104. However, it may further be desired to save a part or all of the procedure to a hard drive device in the hospital information system for the hospital's records. Still further, the surgeon may desire to save a part or all of the procedure directly to a storage device on the surgeon's computer in the surgeon's office. There are many differing configurations that may be specified by the user either before or even during the procedure allowing for maximum system flexibility.

Video monitor(s) 124 are also illustrated connected to computer(s) 122. It should be understood that operating room control system 100 allows for video feeds to remote locations for telesurgery and teleconferencing such that a surgeon at a remote location could view the surgical procedure and provide input or comments to the surgeon performing the procedure. In addition, a video feed could be provided to a classroom environment for educational purposes so that medical students have the opportunity to see a particular medical procedure from a remote location.

Surgical monitor(s) 126 are shown connected to interface 102 and may comprise one or more surgical monitors positioned in the operating room. Typically a main surgical monitor (typically a large (40"-60") flat panel display) is provided in the operating room and quite often numerous surgical monitors are positioned at various locations in the operating room. It is contemplated that the video feed from the video endoscope 110 will be displayed on surgical monitor(s) 126, however, the input devices (touchscreens) allow the user to display virtually any information thereon as desired. While surgical monitor(s) 126 are shown connected to interface 102, it is understood that they may alternatively be directly connected to computer 104.

The opening and closing of various medical procedure sessions and the routing and saving of image data will now be discussed in connection with FIGS. 2-7.

Figure 2:
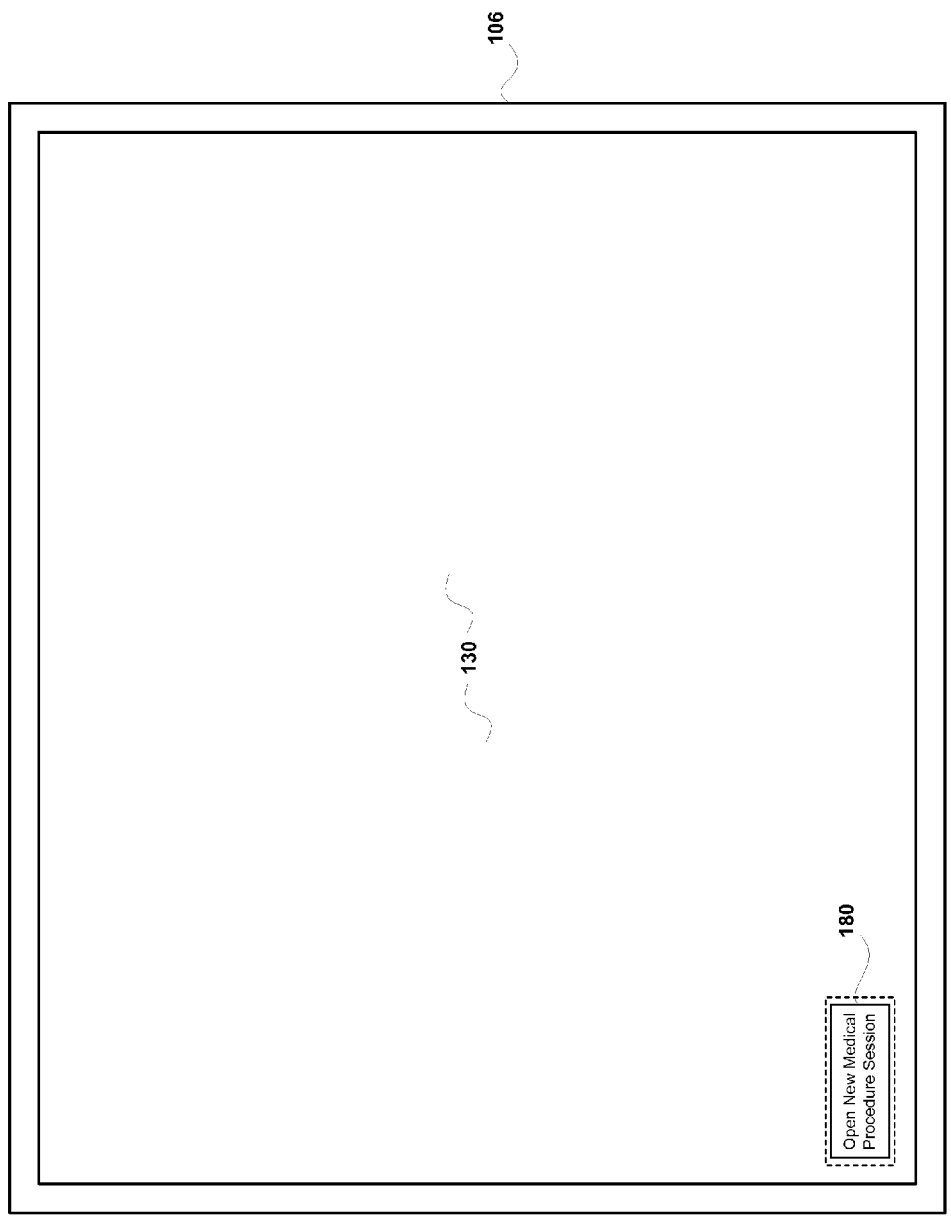
FIG. 2 is an illustration of a touchscreen according to one embodiment of the present invention according to FIG. 1.

FIG. 2 provides a view of input device (touchscreen) 106. While input device (touchscreen) 106 is discussed in connection with the following FIGS, it should be understood that any or all of the description may be applicable to input device (touchscreen) 114. Touchscreen 106 is provided with a front panel 130 on which various data are displayed to the user.

As no medical procedure session has been opened at this point and therefore no configuration of the operating room control system 100 has yet occurred, the front panel 130 is essentially blank with the exception of open new medical procedure session icon 180. Once opened, new medical procedure session icon 180 is activated (shown with dashed line), then the particular type of medical procedure to be performed may be specified and the operating room control system 100 can be configured according to the surgeon's preferences.

Figure 3:
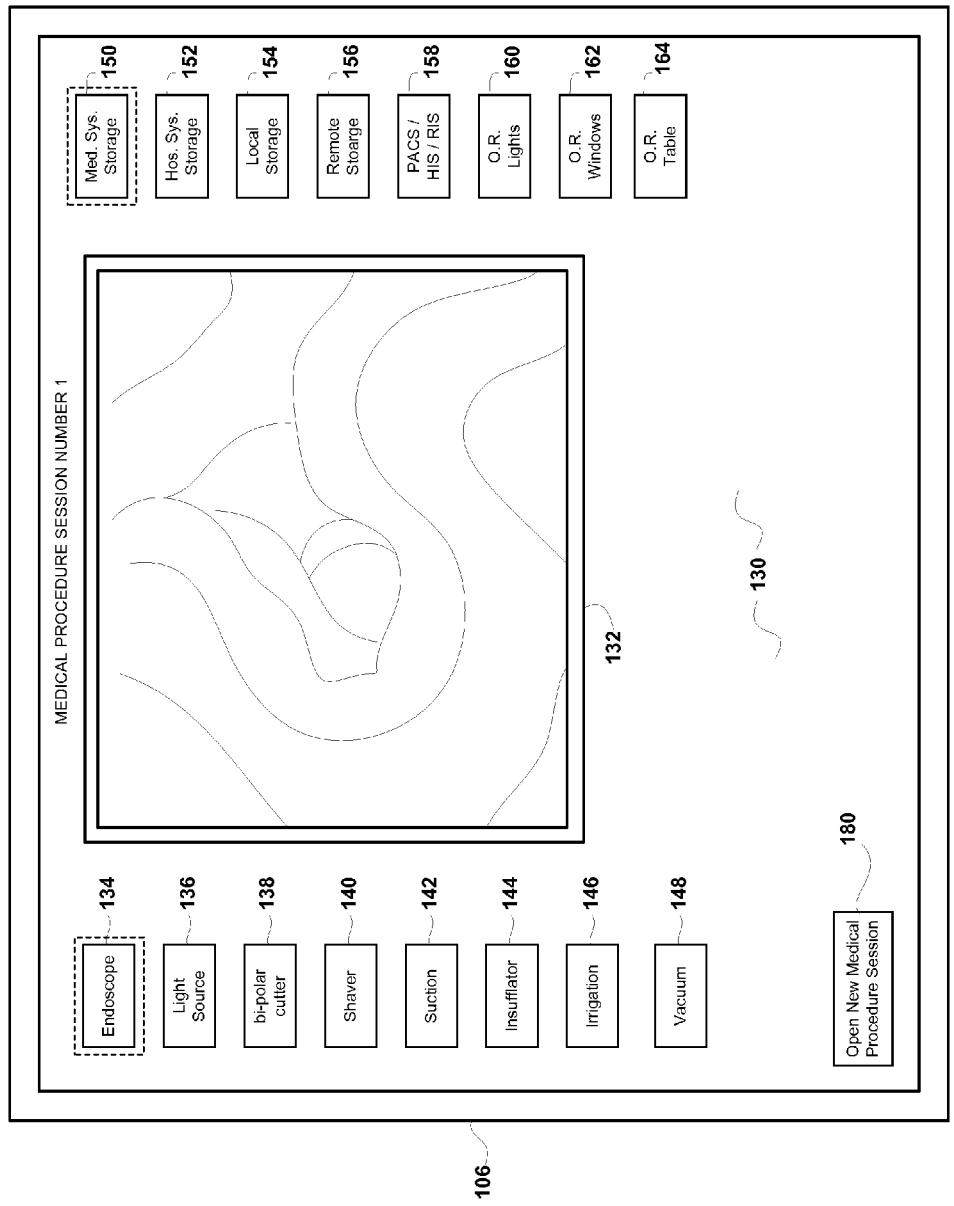
FIG. 3 is an illustration of a touchscreen according the embodiment of FIG. 2.

Referring now to FIG. 3, various data are displayed to the user on front panel 130. For example, in the top center of front panel 130, video display 132 is positioned. Video display 132 will provide the video feed from endoscope 110 such that the user will be able to see a live video feed on the touchscreen 106.

Also shown on front panel 130 are various icons associated with various devices including: endoscope icon 134, light source icon 136, bi-polar cutter icon 138, shaver icon 140, suction icon 142, insufflator icon 144, irrigation icon 146 and vacuum icon 148. These icons are associated with various medical tools and medical equipment. It should be understood that some, all or different icons may be presented on front panel 130 depending on the medical procedure to be performed and those indicated are only provided to exemplify some of the types of devices/equipment that may be connected thereto and used by the surgeon.

On the right side of front panel 130 additional icons are illustrated including: medical system storage 150, hospital system storage 152, local storage 154, remote storage 156, PAC/HIS/RIS 158, operating room lights 160, operating room windows 162 and operating room table 164. Again, it should be understood that while certain types of hospital/medical storage devices and locations/systems and certain types of operating room equipment are listed here, this is not meant to be an exhaustive list as those of skill in the art would understand that many differing types of systems may advantageously be connected to and brought under the control of the operating room control system 100 without deviating from the invention disclosed herein.

At the top of front panel 130 the title "Medical Procedure Session Number 1" is provided as a generic description. It is contemplated that the type of procedure, the name of the patient and/or surgeon, the date, and the like, may be used to describe the particular medical procedure session in progress.

Figure 4:
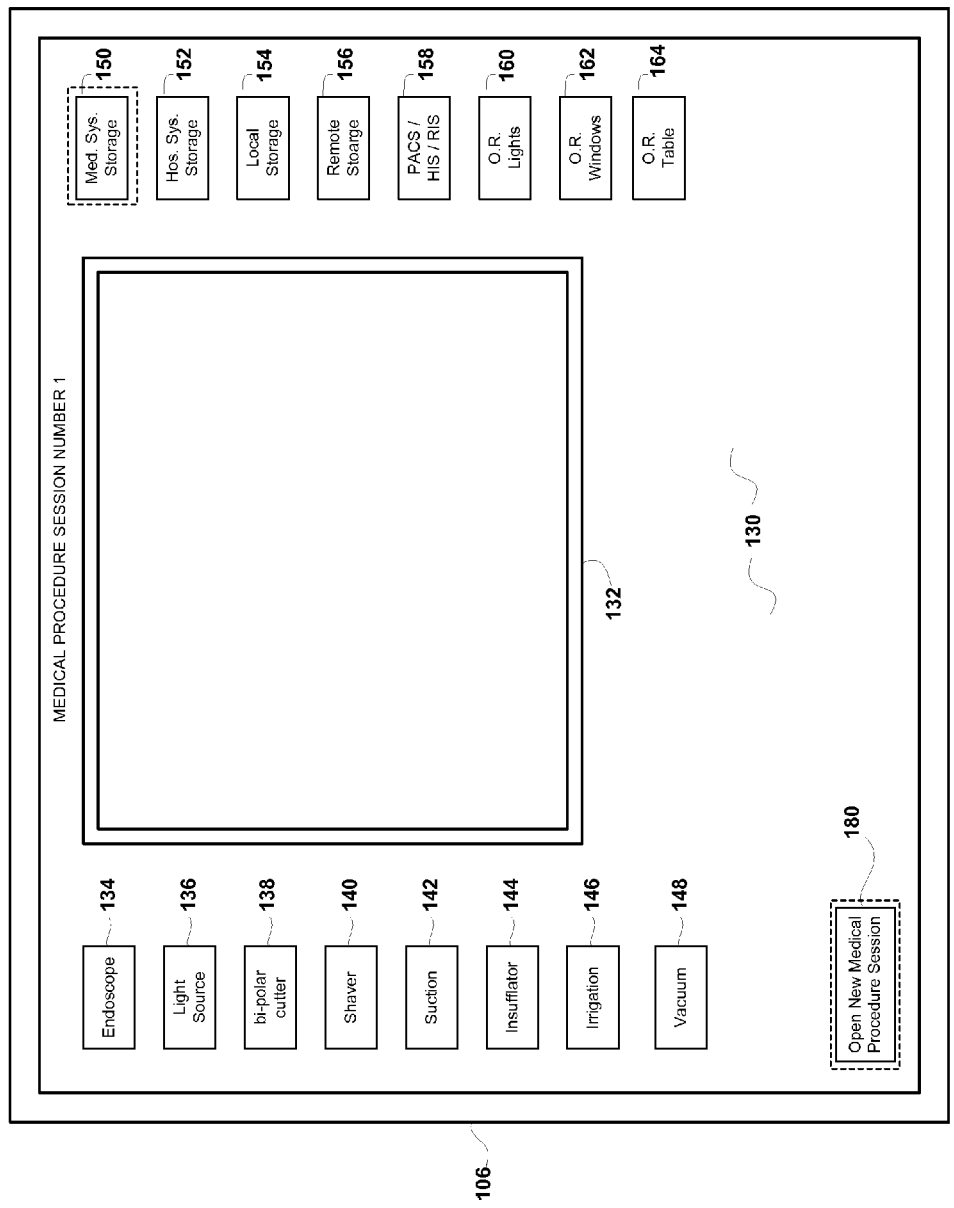
FIG. 4 is an illustration of a touchscreen according the embodiment of FIG. 2.

Referring now to FIG. 4, the touchscreen 106 is shown with the various data and icons as illustrated in FIG. 3, however, the image data is no longer being displayed on the video display 132 as the surgical procedure has been completed. However, as can be seen by the dashed line around the medical system storage icon 150, the image data is still being routed to and stored on the storage device associated with medical system storage icon 150. This may take some time (e.g. writing of the image data to a DVD could take quite some time). In the meantime, even though medical procedure session number one is still open due to the routing and saving of the image data to one or more storage devices, the user is able to activate the open new medical procedure session icon 180 in order to open a new session.

Figure 5:
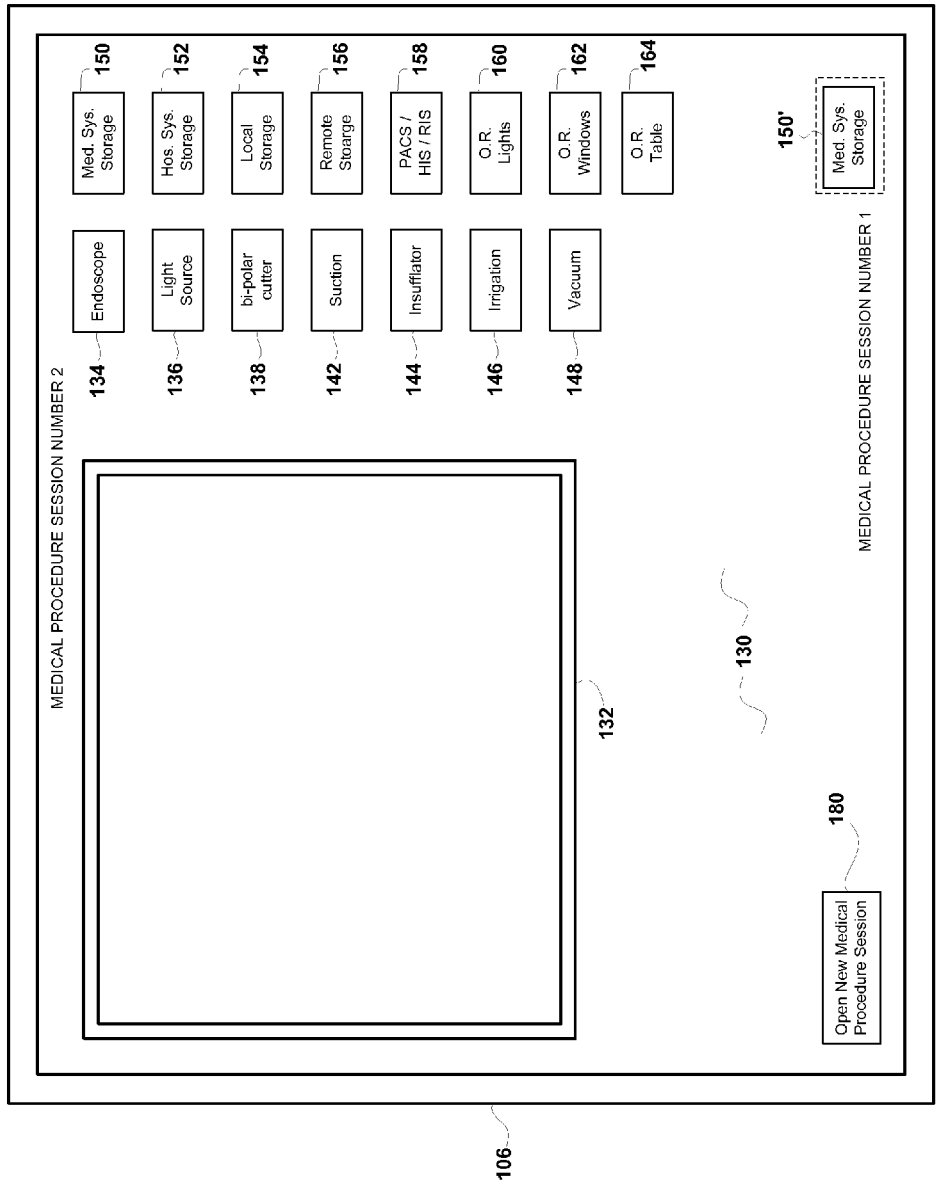
FIG. 5 is an illustration of a touchscreen according the embodiment of FIG. 2.

FIG. 5 illustrates the touchscreen 106 that has been configured for the next medical procedure based on the type of procedure and the surgeon's preferences. The name of the medical session may be provided at the top of the front panel 130 as previously described.

Also shown in FIG. 5 at the bottom of the front panel 130 is an indication that the routing and saving of the image data from the first medical procedure is ongoing and that the first medical procedure session is still open. While an icon 150' labeled medical system storage is shown highlighted at the bottom of the front panel 130, it is contemplated that any type of indication that the routing and saving of the image data from the first medical procedure is ongoing could be utilized. For example, an icon located on a task bar could be used, or a phantom icon adjacent to or behind medical system storage icon 150 could be used, and the like. Likewise, it is understood that any of the storage device icons 152, 154, 156 may be highlighted and written to thereby keeping medical procedure session one open.

Figure 6:
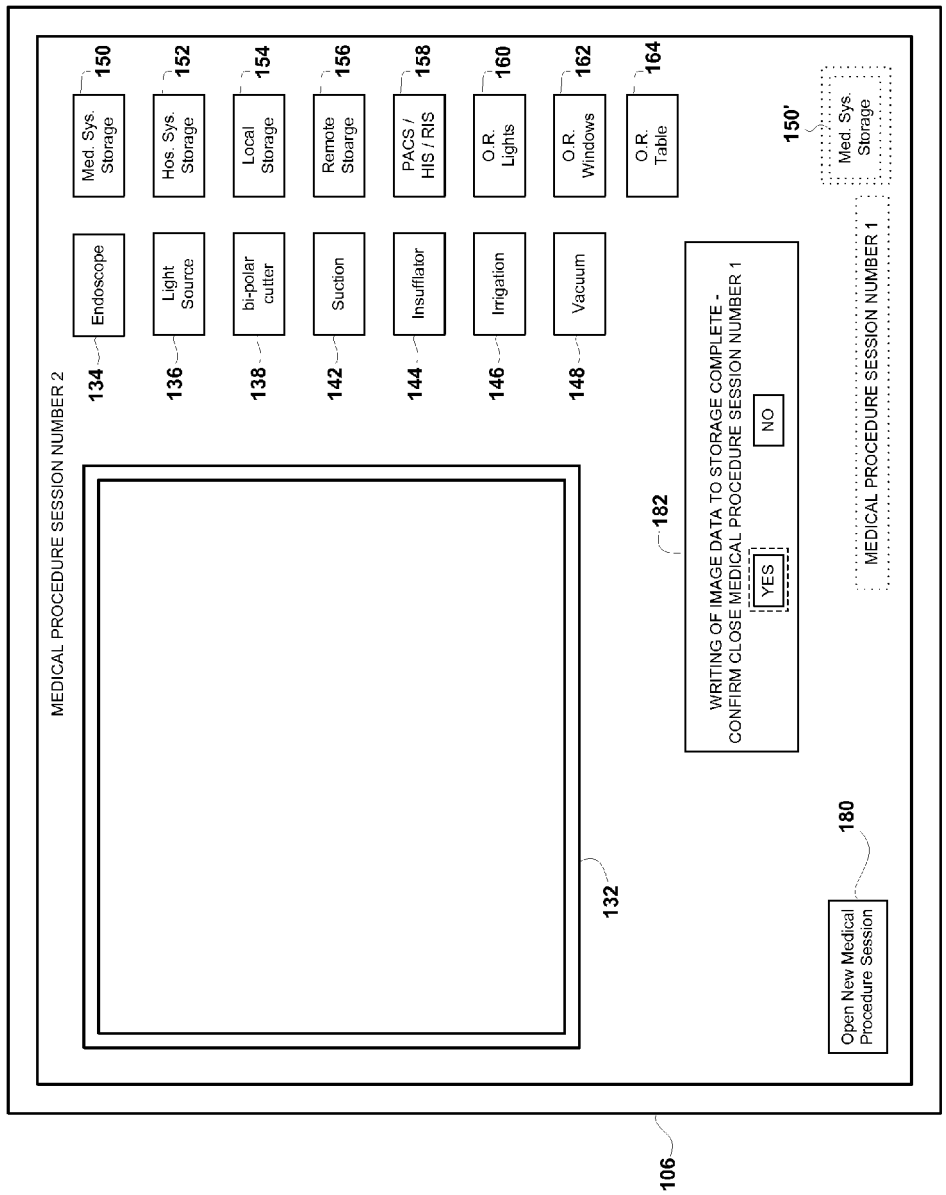
FIG. 6 is an illustration of a touchscreen according the embodiment of FIG. 2.

Turning now to FIG. 6, a notification 182 is presented on front panel 130 that indicates that the routing and saving of the image data to the select storage device(s) is complete and requests confirmation that the medical procedure session number one should be closed. The user need only touch the touchscreen to indicate that the first session is complete. In the event that the user wishes to route and save the image data to another location (e.g. burn a DVD and therefore needs to select local storage) it is understood that a listing of the storage locations may be presented, for example, within the notification 182 such that the user need only touch the desired icon to route the image data to that selected storage location.

Figure 7:
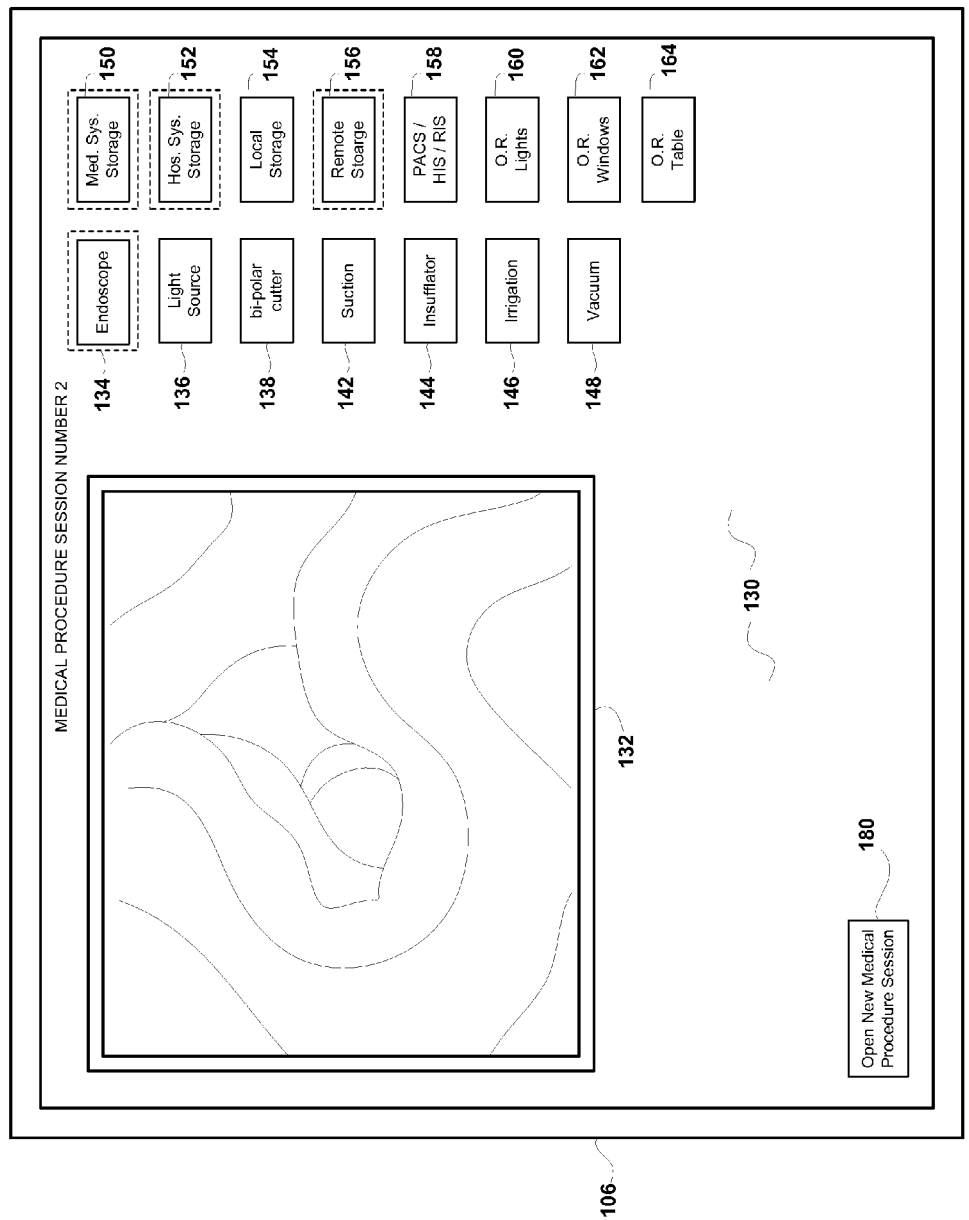
FIG. 7 is an illustration of a touchscreen according the embodiment of FIG. 2.

FIG. 7 illustrates that the second medical procedure is performed and the first medical procedure session is closes.

It should be understood that many variations of the described invention could be introduced without deviating from the present invention. For example, it should be understood that the second medical procedure may be prevented from taking place (e.g. the input and control of the image data, tools and equipment, etc.) until the first medical procedure session is closed. Alternatively, it could be that system allows for the second medical procedure to move forward while the image data from the first medical procedure is being routed and stored. Still further, it could be that image data from multiple surgical procedure sessions is stored in the operating room control system and that routing and storage of image data for all the various medical procedures only occurs after multiple medical procedures are finished (e.g. toward the end of the day).

Likewise, in FIG. 7, the medical system storage icon 150, the hospital system storage icon 152 and the remote storage icon 156 are all highlighted indicating that the user has activated the routing of the image data to the storage locations associated with those icons. The image data may be actively routed and saving to those locations as the medical procedure progresses, or at a later time. The idea is that maximum flexibility is provided to the user in the routing and saving of image data while at the same time, no delay in the setup for the next medical procedure will occur due to the selected routing and saving to the selected storage locations.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An operating room control system comprising:
   a computer having a network connection;
   a storage accessible by said computer;
   an interface unit coupled to said computer;
   an input device coupled to said interface unit;
   a visualization device coupled to said interface unit and generating image data;
   a surgical display coupled to said interface unit and displaying the image data;

software executing on said computer such that a first medical procedure session is opened and the operating room control system is configured for the first medical procedure;

software executing on said computer such that the image data for the first medical procedure session is routed to and saved on said storage;

software executing on said computer such that a second medical procedure session is opened and the operating room control system is configured for the second medical procedure while the image data for the first medical procedure session is being saved on said storage.

2. The operating room control system according to claim 1 wherein when the saving of the image data to said storage is completed, the first medical procedure session is closed by means of software executing on said computer.

3. The operating room control system according to claim 1 wherein said storage comprises a plurality of storage devices selected from the group consisting of:

solid state hard drives, magnetic hard drives, optical devices, removable storage devices and combinations thereof.

4. The operating room control system according to claim 1 wherein the configuration of the operating room control system for the first medical procedure session is different than the configuration of the operating room control system for the second medical procedure session.

5. The operating room control system according to claim 4 further comprising at least one medical tool and at least one piece of medical equipment coupled to said interface unit, said interface unit providing both communication between said at least one medical tool and said computer and between said at least one piece of medical equipment and said computer, wherein the configuration of the operating room control system for the first medical procedure session includes configuring a setting for the at least one medical tool and at least one piece of medical equipment.

6. The operating room control system according to claim 5 wherein the setting for the at least one medical tool and at least one piece of medical equipment comprises a first medical tool setting and a first medical equipment setting, and the configuration of the operating room control system for the second medical procedure session includes configuring a second medical tool setting and second medical equipment setting.

7. The operating room control system according to claim 6 wherein at least one of the first medical tool setting and the second medical tool setting are different; or the first medical equipment setting and the second medical equipment setting are different.

8. The operating room control system according to claim 1 wherein the input device comprises a touchscreen and the first medical procedure session is opened by activation of the touchscreen.

9. The operating room control system according to claim 8 wherein the second medical procedure session is opened by activation of the touchscreen.

10. The operating room control system according to claim 9 wherein the first medical procedure session is closed by activation of the touchscreen.

11. The operating room control system according to claim 10 wherein the touchscreen comprises a first touchscreen positioned in the sterile environment, the system further comprising a second touchscreen coupled to said interface unit, the second touchscreen providing the functionality of the first touchscreen.

12. The operating room control system according to claim 11 wherein the second touchscreen is located outside of the sterile environment.

13. A method for configuring an operating room control system including: a computer connected to a network, a storage accessible by the computer, an interface unit connected to the computer, and an input device and a visualization device both connected to the interface unit, the method comprising the steps of:

executing software on the computer to open a first medical procedure session on the operating room control system;

configuring the operating room control system based on the type of medical procedure to be performed and according to predefined configuration preferences;

generating image data for the first medical procedure session with the visualization device;

routing the image data to the storage;

saving the image data on to the storage;

executing software on the computer to open a second medical procedure session on the operating room control system while simultaneously saving the image data for the first medical procedure session on the storage;

executing software on the computer to close the first medical procedure session on the operating room control system when the image data has been saved on the storage.

14. The method according to claim 13 wherein the configuration of the operating room control system for the first medical procedure session is different than the configuration of the operating room control system for the second medical procedure session.

15. The method according to claim 13 wherein the input device is a touchscreen and the first medical procedure session is opened by activation of the touchscreen and the second medical procedure session is opened by activation of the touchscreen.

16. The method according to claim 15 wherein the closing of the first medical procedure session is confirmed by activation of the touchscreen.

17. The method according to claim 13 wherein the operating room control system includes at least one medical tool and at least one piece of medical equipment connected to said interface unit and wherein said method further comprises providing both communication between said at least one medical tool and said computer and between said at least one piece of medical equipment and said computer via said interface unit.

* * * * *